(12) United States Patent
Baba et al.

(10) Patent No.: US 11,543,421 B2
(45) Date of Patent: Jan. 3, 2023

(54) SPECIMEN PROCESSING SYSTEM

(71) Applicant: HITACHI HIGH-TECH CORPORATION, Tokyo (JP)

(72) Inventors: Shunsuke Baba, Tokyo (JP); Kuniaki Onizawa, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 372 days.

(21) Appl. No.: 16/647,117

(22) PCT Filed: Nov. 26, 2018

(86) PCT No.: PCT/JP2018/043415
§ 371 (c)(1),
(2) Date: Mar. 13, 2020

(87) PCT Pub. No.: WO2019/142497
PCT Pub. Date: Jul. 25, 2019

(65) Prior Publication Data
US 2021/0018524 A1 Jan. 21, 2021

(30) Foreign Application Priority Data
Jan. 16, 2018 (JP) .............................. JP2018-004998

(51) Int. Cl.
*G01N 35/00* (2006.01)
*G01J 5/00* (2022.01)
(Continued)

(52) U.S. Cl.
CPC .......... *G01N 35/00613* (2013.01); *G01J 5/00* (2013.01); *G01M 99/005* (2013.01);
(Continued)

(58) Field of Classification Search
CPC ........ G01N 35/00613; G01N 35/00722; G01J 5/00; G01M 99/005
See application file for complete search history.

(56) References Cited

U.S. PATENT DOCUMENTS

| 10,768,186 B2 * | 9/2020 | Takaya .................. G01N 35/04 |
| 11,087,876 B2 * | 8/2021 | Dejima .................. G16H 40/63 |

(Continued)

FOREIGN PATENT DOCUMENTS

| JP | 2004-219352 A | 8/2004 |
| JP | 2006-71359 A | 3/2006 |

(Continued)

OTHER PUBLICATIONS

International Preliminary Report on Patentability dated Jul. 30, 2020, received in corresponding International Application No. PCT/JP2018/043415.

(Continued)

*Primary Examiner* — Bryan Bui
(74) *Attorney, Agent, or Firm* — Mattingly & Malur, PC

(57) ABSTRACT

A specimen processing system 100 which performs preprocessing and analysis of a specimen includes sensors 5a, 5b, ... each detecting a driving state of a driving device installed in the system, an abnormality detecting part 3a determining from signal waveforms detected by the sensors 5a, 5b, ... whether an abnormality occurs in the driving device, and a recording device sequentially recording the signal waveforms detected by the sensors 5a, 5b, ... and storing a sensor signal waveform before or after the occurrence of an operation abnormality into an unerasable area when the abnormality is determined to have occurred in the abnormality detection part 3a. Consequently, there is provided a speci- (Continued)

men processing system capable of realizing restoration from the time of the occurrence of an abnormality faster than in the past.

10 Claims, 8 Drawing Sheets

(51) Int. Cl.
  *G01M 99/00* (2011.01)
  *G01N 21/59* (2006.01)
  *G01N 33/49* (2006.01)
  *G01N 33/493* (2006.01)
  *G01J 5/48* (2022.01)

(52) U.S. Cl.
  CPC .............. *G01N 21/59* (2013.01); *G01N 33/49* (2013.01); *G01N 33/493* (2013.01); *G01N 35/00722* (2013.01); *G01J 5/48* (2013.01); *G01J 2005/0077* (2013.01)

(56) References Cited

U.S. PATENT DOCUMENTS

| | | | |
|---|---|---|---|
| 2006/0046299 | A1 | 3/2006 | Nishikiori et al. |
| 2015/0044096 | A1* | 2/2015 | Nakasawa ............ G01N 35/025 422/64 |
| 2018/0052183 | A1 | 2/2018 | Takaya et al. |

FOREIGN PATENT DOCUMENTS

| | | | |
|---|---|---|---|
| JP | 2007-225525 A | | 9/2007 |
| JP | 2008-2898 A | | 1/2008 |
| JP | 2009-210318 A | | 9/2009 |
| JP | 2010-48758 A | | 3/2010 |
| JP | 2013-148445 A | | 8/2013 |
| JP | 2013148445 A | * | 8/2013 |
| JP | 2014-149779 A | | 8/2014 |
| WO | 2016/147714 A1 | | 9/2016 |

OTHER PUBLICATIONS

International Search Report of PCT/JP2018/043415 dated Feb. 26, 2019.
Extended European Search Report received in corresponding European Application No. 18900947.5 dated Sep. 16, 2021.

* cited by examiner

SPECIMEN PROCESSING SYSTEM

TECHNICAL FIELD

The present invention relates to an automatic analyzer which analyzes specimens such as blood, urine, and a specimen preprocessing device which performs preprocessing precedent to analysis on the specimens (collectively referred to as a specimen processing system).

BACKGROUND ART

With a view toward remotely managing a clinical specimen processing device by a technician or the like in a support center, there has been described in Patent Literature 1, a remote management method of remotely managing a clinical specimen processing device processing a clinical specimen, in which the clinical specimen processing device is captured by an imaging device, and a captured image captured by the imaging device is provided from the imaging device to a managing device provided in a remote site of the clinical specimen processing device through a communication network to display a captured image in the managing device.

Further, with a view toward rapidly and appropriately specifying the cause of occurrence of a failure in an automatic analyzer, there have been described in Patent Literature 2 that a storage unit is provided which stores an alarm log of recording information about the failure caused in the device, an operation log of recording information about an operation applied to the device, a communication log of recording information communicated within the device, and an analysis abnormality log of recording information about an abnormality in an analysis result by the device, and that at least some records included in each of the alarm log, the operation log, the communication log, and the analysis abnormality log are connected to thereby create one composite file, the record relatable to the cause of occurrence of the failure is retrieved from within the records recorded in the composite file, and when the record relatable to the cause of occurrence of the failure exists as its retrieval result, the designation input of a record to be reproduced by the corresponding device within the composite file is received, and an operation having the same content as the designated and input record is executed.

Citation List

Patent Literature

PTL 1: Japanese Unexamined Patent Application Publication No. 2006-71359
PTL 2: Japanese Unexamined Patent Application Publication No. 2008-2898

SUMMARY OF INVENTION

Technical Problem

As a specimen processing system for automatically performing the analysis of biological specimens such as blood, urine, etc., there are a specimen preprocessing device which performs charging, centrifugation, dispensing, labeling, etc. on specimens such as blood, urine collected for testing, and an automatic analyzing device which analyzes the specimens processed by such a specimen preprocessing device.

There are many types of processing and analyses performed by these specimen preprocessing device and automatic analyzing device. Therefore, there is used a specimen processing system in which each processing is set as a separate (analysis) unit, and which is connected via a specimen transfer line transferring a specimen between those processing (analysis) units.

In the specimen processing system, a motor or the like is used to transport and process a specimen container for blood, urine and the like to thereby control a drive system of a device. In dealing with the specimen by the device, a specimen container, a rack with the specimen container placed thereon, a device's drive system, etc. are detected by a sensor.

In the above-described specimen processing system, there is a case where a specimen processing operation cannot be executed when a device abnormality occurs. Since, however, an inspection result is necessary for determination of treatment policy, restoring from the abnormality is early required when the device abnormality has occurred.

When the device abnormality occurs in the specimen processing system, a device alarm informs an operator of the device abnormality. In order to specify the cause of the device abnormality, sensor information of the device and the like are confirmed to thereby perform a device investigation.

It is now the mainstream that sensor information acquirable as information before or after the occurrence of a device abnormality when the device abnormality occurs is acquired using a log function of an on/off state. Therefore, in order to specify the cause of the device abnormality, there is a need to observe a signal waveform of the sensor by using a signal observing apparatus. It thus takes time to restore the state of the device.

In order to solve this problem, there is a need to improve a method of acquiring information of a device situation.

Patent Literature 1 described above is accompanied by a problem that it is the remote management method of displaying the image obtained by the imaging device via the communication network, but is not a method of acquiring device information leading to the investigation of the basic cause upon the device abnormality, whereby the time necessary for investigation in finding the cause becomes long.

Further, Patent Literature 2 is accompanied by a problem that since it is a method of acquiring the analysis abnormality log in the automatic analyzer as information, but does not show information indicating the device state related to the device abnormality and at the abnormality related to the operation/control of the device, it takes time to investigate the cause of the operation abnormality of the device.

There has thus been a demand for development of a technique which contributes to rapid restoration.

An object of the present invention is to provide a specimen processing system capable of realizing restoration from the time of the occurrence of an abnormality faster than before.

Solution to Problem

The present invention includes a plurality of means for solving the above problems but, if an example thereof is given, is a specimen processing system which performs preprocessing and analysis of a specimen. The specimen processing system including sensors each detecting a driving state of a driving device installed in the system, and an abnormality detecting part determining from signal waveforms detected by the sensors whether an abnormality occurs in the driving device, is characterized by including a recording device which sequentially records the signal waveforms detected by the sensors, and stores a sensor signal waveform before or after the occurrence of an operation abnormality into an unerasable area when the abnormality is determined to have occurred in the abnormality detecting part.

Advantageous Effects of Invention

According to the present invention, since a method of acquiring device information can be improved, it is possible to realize restoration from the time of occurrence of an abnormality faster than before. Issues, configurations, and effects other than those described above will be clarified by the following description of embodiments.

DESCRIPTION OF EMBODIMENTS

Hereinafter, embodiments of a specimen processing system of the present invention will be described using the drawings.

First Embodiment

A first embodiment of a specimen processing system of the present invention will be described using FIGS. 1 through 4.

Figure 1:
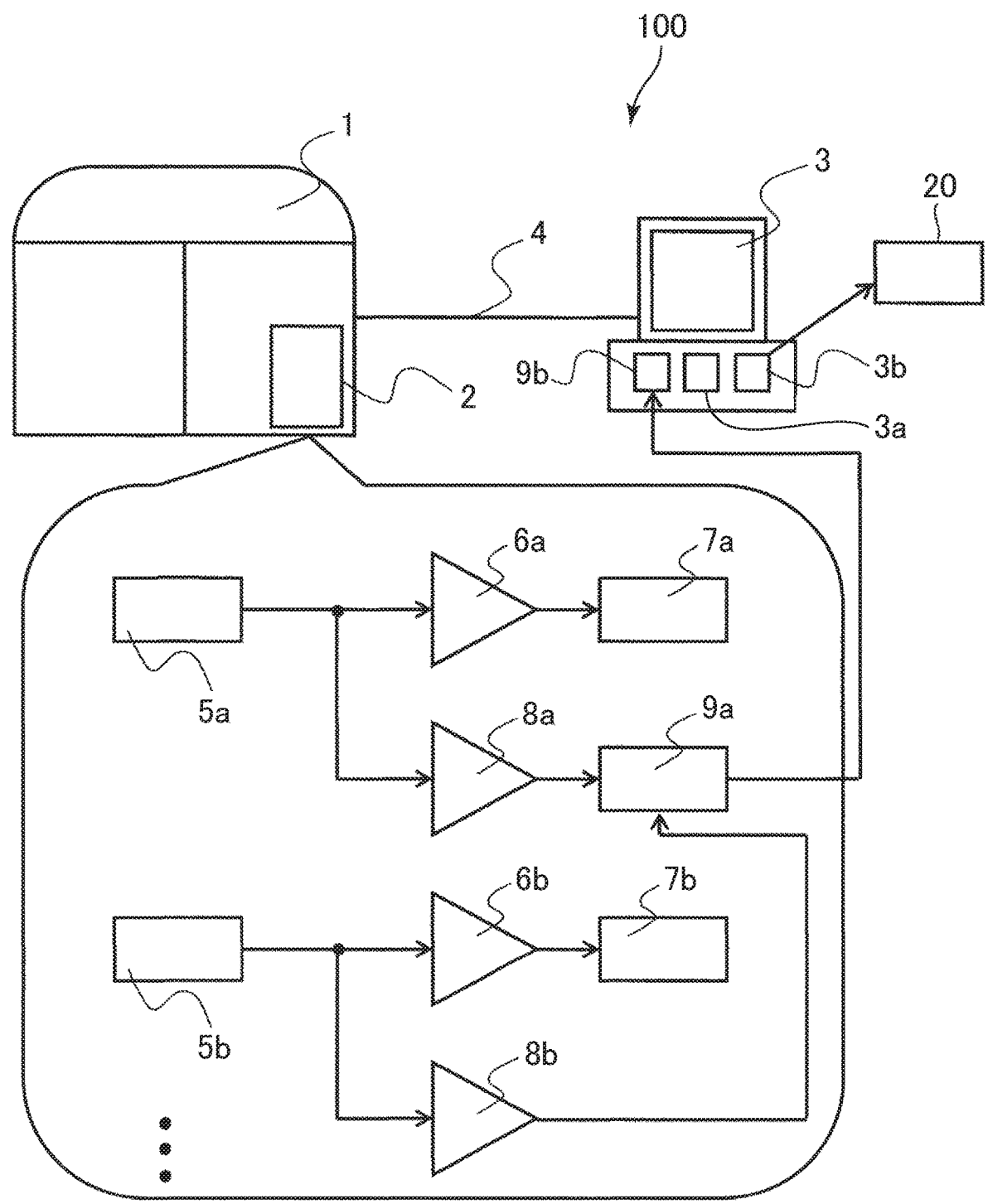
FIG. 1 is a typical diagram of a specimen processing device having a sensor signal observing function according to a first embodiment of the present invention.
Figure 2:
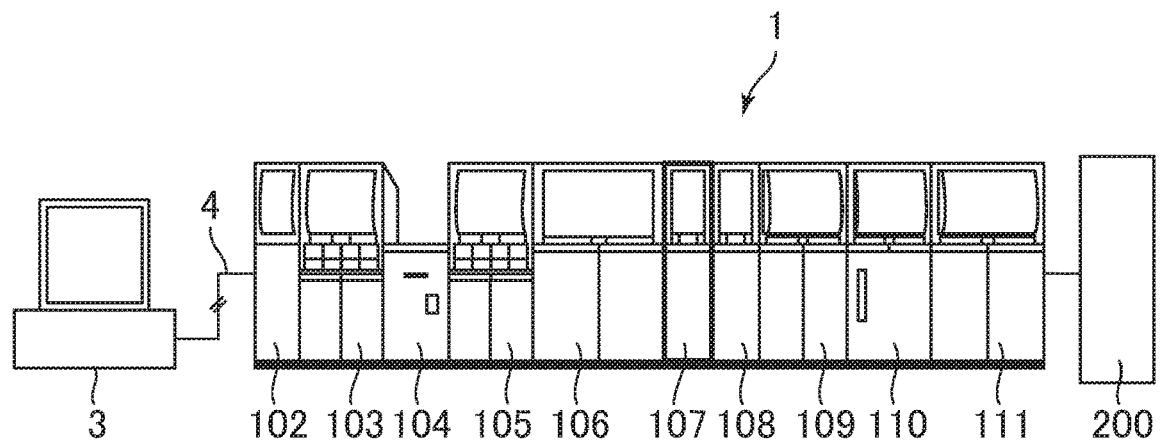
FIG. 2 is a diagram showing an example of an external appearance of a specimen preprocessing device which is an example of the specimen processing device according to the first embodiment.
Figure 3:
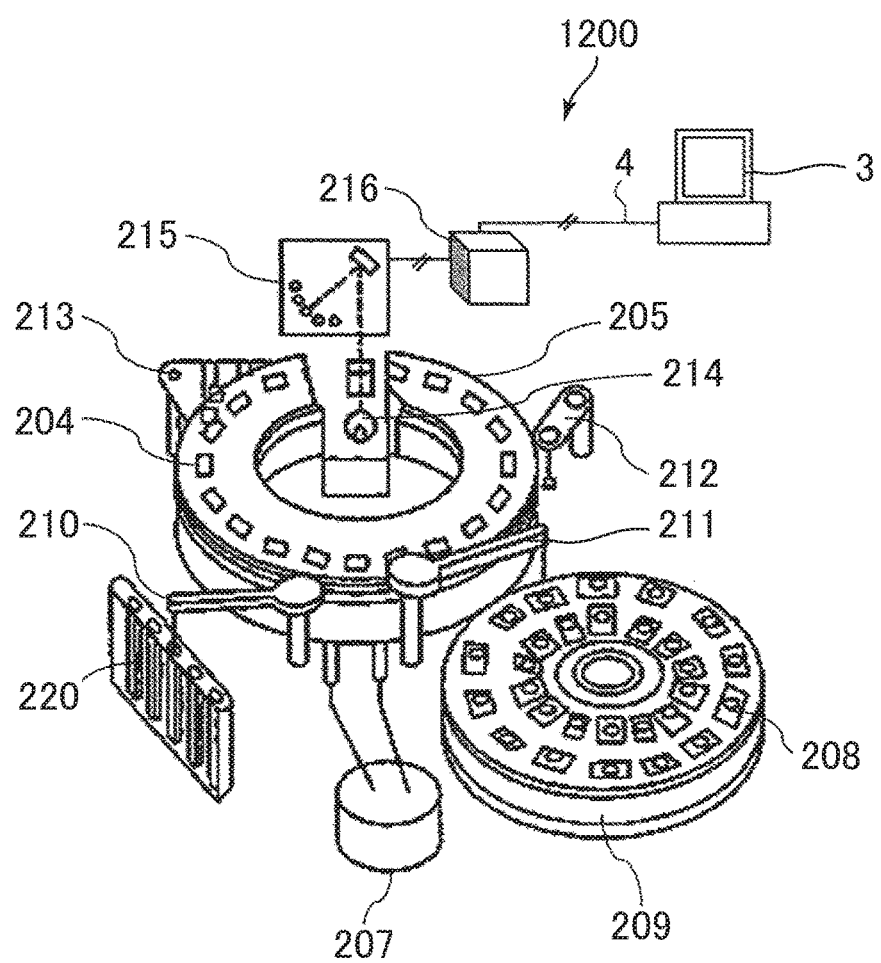
FIG. 3 is a diagram showing an example of the outline of a biochemical automatic analyzer being an example of the specimen processing device according to the first embodiment.

First, an overall configuration of the specimen processing system will be described using FIGS. 1 through 3. FIG. 1 is a diagram showing a typical example of the specimen processing system according to the present embodiment. FIG. 2 is a diagram showing an example of an external appearance of a specimen preprocessing device being an example of a specimen processing device, and FIG. 3 is a diagram showing an example of the outline of a biochemical automatic analyzer being another example of the specimen processing device.

In FIG. 1, the specimen processing system 100 which preprocesses and analyzes a specimen includes a specimen processing device 1, a sensor signal observing substrate 2, an operation unit PC3, a communication connection line 4, etc.

The specimen processing device 1 which treats specimens such as blood, urine has the sensor signal observing substrate 2. Such a specimen processing device 1 is, for example, an automatic analyzer which performs a biochemical analysis, an immune analyzer which performs an immunological analysis, or a specimen preprocessing device connected to the automatic analyzer and the immune analyzer.

Hereinafter, one example of the specimen preprocessing device will be described using FIG. 2.

In FIG. 2, as viewed from the left side to the right side in FIG. 2, the specimen processing device 1 is comprised of a plurality of units having as basic elements, a closing unit 102, a specimen storage unit 103, an empty holder stacker 104, a specimen input unit 105, a centrifugal unit 106, a liquid amount measuring unit 107, an opening unit 108, a child specimen test-tube preparation unit 109, a dispensing unit 110, and a transfer unit 111, and an operation unit PC3 which controls the operations of these plural units.

An automatic analyzer 200 for performing qualitative and quantitative analyses of the components of a specimen is connected as a transfer destination of the specimen processed by the specimen processing device 1.

The specimen input unit 105 is a unit for inputting a specimen container 200 (refer to FIG. 3) in which the specimen is stored. The centrifugal unit 106 is a unit for performing centrifugation on the input specimen container 220. The liquid amount measuring unit 107 is a unit which performs liquid amount measurement of the specimen stored in the specimen container 220. The opening unit 108 is a unit which opens a stopper of the input specimen container 220. The child specimen test-tube preparation unit 109 is a unit which performs necessary preparations necessary to dispense the specimen stored in the input specimen container 220 into the next dispensing unit 110. The dispensing unit 110 is a unit which subdivides the centrifuged specimen into small specimens for analyzing the same by the automatic analyzer 200, and attaches barcodes or the like to the specimen containers 220 and child specimen containers 220 subjected to the subdivision. The transfer unit 111 classifies the dispensed child specimen containers 220 and performs transfer preparations for the automatic analyzer 200. The closing unit 102 is a unit which closes the stopper against the specimen containers 220 and the child specimen containers 220. The specimen storage unit 103 is a unit which stores each closed specimen container 220.

Hereinafter, one example of the configuration of the biochemical automatic analyzer will be descried in brief using FIG. 3.

The device shown in FIG. 3 is the specimen processing device 1 shown in FIG. 1 or the automatic analyzer 200 shown in FIG. 2.

In FIG. 3, the specimen processing device 1 or the automatic analyzer 200 is a part measuring the concentration of a biological component contained in the specimen, and has a reaction container 204, a reaction disk mechanism 205, a thermostatic tank 207, a reagent magazine 209, a specimen dispensing mechanism 210, a reagent dispensing mechanism 211, a stirring mechanism 212, a cleaning mechanism 213, a light source 214, a photometer 215, and an A/D (Analog/Digital) converter 216.

The reaction container 204 is a container filled with a reagent and a specimen to react with each other.

The reaction disk mechanism 205 is a member which holds a plurality of reaction containers 204. Further, the reaction disk mechanism 205 transfers each reaction container 204 installed to itself to a designated position.

The thermostatic tank 207 is a mechanism for keeping the reaction container 204 installed in the reaction disk mechanism 205 at a predetermined temperature, and holds the reaction container 204 at the predetermined temperature.

The reagent magazine 209 is a member holding a plurality of reagent bottles 208 each being a container storing a reagent used for analysis. Further, the reagent magazine 209 transfers the reagent bottle 208 installed to itself to a designated position.

The specimen dispensing mechanism 210 is a device which is provided with a specimen dispensing probe and divides the specimen into fixed amounts little by little. The specimen dispensing mechanism 210 dispenses the specimen put in the specimen container 220 into each reaction container 204 by a prescribed amount.

The reagent dispensing mechanism 211 is a device which is provided with a reagent dispensing probe and divides the reagent into fixed amounts little by little. The reagent dispensing mechanism 211 dispenses the reagent put in the reagent bottle 208 into each reaction container 204 by a prescribed amount.

The stirring mechanism 212 stirs a solution of the reagent and specimen put in the reaction container 204 to uniformize a distribution state of components thereof.

The cleaning mechanism 213 is a device which performs aspiration of waste liquid and discharge of cleaning liquid. The cleaning mechanism 213 aspirates the solution of the reagent and specimen put in the reaction container 204. Also, the cleaning mechanism 213 discharges the cleaning liquid into the reaction container 204 to clean the reaction container 204.

The light source 214 is a part which emits light used for absorbance measurement and is comprised of a halogen lamp, an LED or the like.

The photometer 215 is a part which receives light emitted from the light source 214 and transmitted through the reaction container 204 and measures the absorbance of the solution in the reaction container 204, and is comprised of a spectrophotometer or the like. The photometer 215 transmits information about the absorbance to the A/D converter 216.

The A/D converter 216 is a device which converts an analog signal into a digital signal. After the A/D converter 216 converts the input analog signal into the digital signal, it records the same in a recording medium 9b or the like of the operation unit PC3.

The sensor signal observing substrate 2 disposed in the above-described specimen processing device 1 has sensors 5a, 5b, . . . , comparators 6a, 6b, . . . , control ICs 7a, 7b, . . . , AD converters 8a, 8b, . . . , and a recording memory 9a.

The sensor signal observing substrate 2 converts signals output from the sensors 5a, 5b, . . . disposed in plural form within the specimen processing device 1 into on/off signals through the individual comparators 6a, 6b, . . . and outputs them to the individual control ICs 7a, 7b, . . . . They are used for device drive control in the operation unit PC3 to be described later.

The sensors 5a, 5b, . . . are sensors each of which detects a driving state of a driving device installed in the specimen processing device 1.

In the present invention, the devices each targeted for detecting the driving states by the sensors 5a, 5b, . . . are various devices to be driven within the specimen processing system 100.

There are various devices such as a driving motor driving a conveying belt which conveys the specimen container 220 with the specimen in the specimen processing device 1 stored therein among the respective units in the specimen preprocessing device shown in FIG. 2, a motor driving a stopper to stop the specimen container 220 with such transfer units, a rotating motor for the centrifugal unit 106, a pump connected to a dispensing mechanism (the dispensing unit 110 shown in FIG. 2, and the specimen dispensing mechanism 210 and the reagent dispensing mechanism 211 shown in FIG. 3) used upon specimen dispensation and reagent dispensation, a motor which rotatably drives the reagent magazine 209 storing the reagent therein, a cooling container used when cooling the reagent magazine 209, etc.

Further, in the sensor signal observing substrate 2, the signal waveforms output from the sensors 5a, 5b, . . . are input to the individual AD converters 8a, 8b, . . . without via the comparators 6a, 6b, . . . to thereby convert the sensor signals from analog to digital.

In the sensor signal observing substrate 2, the individual signal waveforms of the respective sensors 5a, 5b, . . . after the AD conversion are sequentially stored and recorded in the recording memory 9a. It is also possible to save the stored signal waveforms for a prescribed time and erase unnecessary data.

The operation unit PC3 controls the operation of each mechanism in the specimen processing device 1 and also executes arithmetic processing of an analytical result of the specimen, etc. The specimen processing device 1 and the operation unit PC3 are connected to each other by the communication connection line 4. The operation unit PC3 has an abnormality detecting part 3a, a communication part 3b, and the recording medium 9b.

The abnormality detecting part 3a determines from the signal waveforms of the on/off signals detected by the sensors 5a, 5b, . . . and converted by the comparators 6a, 6b, . . . whether it is necessary to generate a device alarm with the occurrence of an abnormality in each driving device in the specimen processing device 1. When it is determined that the abnormality has occurred, the abnormality detecting part 3a generates a device alarm and outputs the same to the communication part 3b and the sensor signal observing substrate 2 or the like. An abnormality determination method can be carried out by the known method.

The communication part 3b is a network device enabling communication with the outside, which in response to the input of the device alarm from the abnormality detecting part 3a, outputs sensor signal waveform information before or after the occurrence of an operation abnormality to the side of a maintenance person who maintains the specimen processing system 100. The maintenance person confirms the state of the abnormality of the specimen processing device 1 through a maintenance-person side display device 20.

The recording medium 9b is a recording device which is provided physically away from the recording memory 9a and stores the sensor signal waveform before or after the occurrence of the operation abnormality upon receipt of the input of the device alarm from the abnormality detecting part 3a. The sensor signal waveform before or after the occurrence of the operation abnormality recoded in the recording medium 9b is assumed to be unerasable.

Incidentally, the term "before or after the occurrence of the operation abnormality" is, for example, a value of several hundred seconds before or after the time of the occurrence of the abnormality, etc. but can be set as appropriate according to the amount of information. Values different for each device can be set according to the kind of the driving device targeted for monitoring, or the like.

The recording device is comprised of the recording medium 9b and the recording memory 9a. The recording memory 9a and the recording medium 9b are respectively comprised of a known recording device such as a RAM, an HDD, an SSD or the like.

Figure 4:
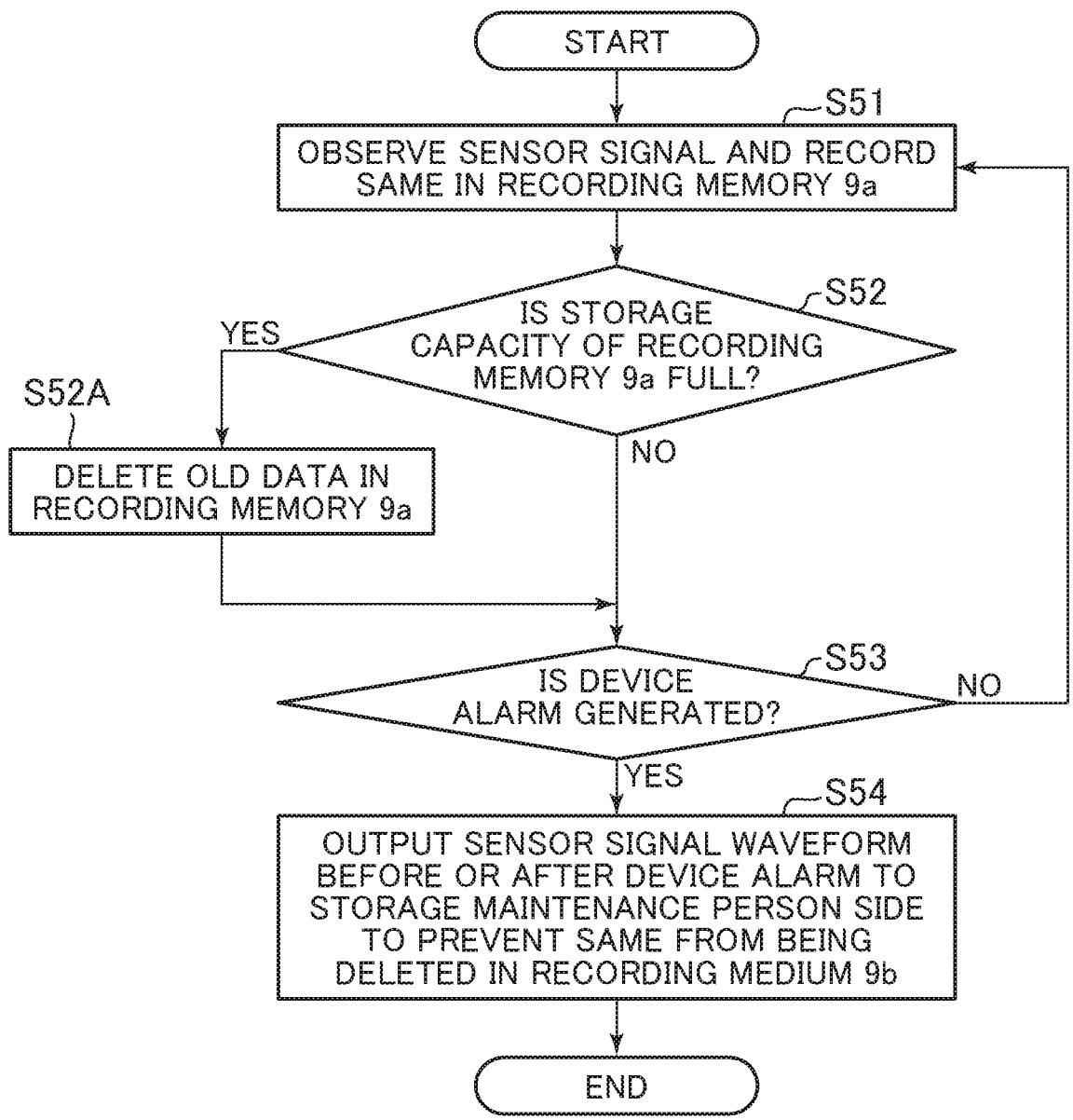
FIG. 4 is a diagram showing a processing flow of the specimen processing device according to the first embodiment.

Next, the operation of the specimen processing system according to the present embodiment will be described with reference to FIG. 4. FIG. 4 is a processing flow of the specimen processing device having the sensor signal observing function according to the present invention.

First, in FIG. 4, the specimen processing device 1 observes sensor signal waveforms by means of the sensors 5a, 5b, . . . of the sensor signal observing substrate 2 and records the sensor signal waveforms in the recording memory 9a (Step S51).

Next, the sensor signal observing substrate 2 determines whether or not the recording capacity of the recording memory 9a is full (Step S52). When it is determined that the recording capacity is full, the processing is advanced to Step S52A, where old data in the recording memory 9a is deleted to ensure a recordable area (Step S52A). For example, only data before or after the abnormality occurrence or data allowed to have an extension, which is to be stored in the recording medium 9b is left, and data before that can be deleted, but the amount of its deletion can be set as appropriate. On the other hand, when it is determined that the recording memory 9a is not full, the processing is advanced to Step S53 without deleting the data.

Next, the abnormality detecting part 3a of the operation unit PC3 determines whether it is necessary to generate a device alarm with the occurrence of an abnormality in each driving device in the specimen processing device 1 (Step S53). When it is determined that the device alarm is not required, the processing is returned to Step S51, where the observation of each sensor signal waveform is continuously performed.

On the other hand, when it is determined in Step S53 that the device alarm has occurred, the processing is advanced to Step S54, where the specimen processing device 1 is controlled through the communication connection line 4 to store the sensor signal waveform before or after the device alarm recorded in the recording memory 9a in the recording medium 9b being the undeleted area (Step S54). An operator acquires the stored data through the operation unit PC3 and uses it upon executing the analysis of an abnormality in the device. Further, in the present Step S54, the sensor signal waveform information before or after the occurrence of the operation abnormality is output to the side of the maintenance person who maintains the specimen processing system 100 through the communication part 3b.

Next, effects of the present embodiment will be described.

The above-described specimen processing system 100 according to the first embodiment of the present invention, which performs preprocessing and analysis of the specimen, includes the sensors 5a, 5b, . . . each of which detects the driving state of each driving device installed in the system, the abnormality detecting part 3a which determines from the signal waveforms detected by the sensors 5a, 5b, . . . whether the abnormality occurs in the driving device, and the recording device which sequentially records the signal waveforms detected in the sensors 5a, 5b, . . . and stores the sensor signal waveforms before or after the occurrence of the operation abnormality in the unerasable area when it is determined in the abnormality detecting part 3a that the abnormality has occurred.

In the specimen processing system 100 restored early from the abnormality and required to early resume a specimen processing operation when the device abnormality has occurred, the signal waveforms of the sensors 5a, 5b, . . . in the device are observed, and the sensor signal waveforms before or after the time of the occurrence of the abnormality are recorded in unerasable form when the device abnormality has occurred, whereby it is not necessary to confirm the sensor signal waveforms by attaching a data logger or the like for the analysis of the state after the device alarm. For this reason, the information necessary to investigate the cause of the device abnormality always exists in the device, and hence information about the device abnormality can be acquired appropriately and rapidly. It is thus possible to quicken phenomenon analysis of the device abnormality, shorten the time taken for state restoration, and shorten a non-operating time in the specimen processing system. Such rapid restoration from the device abnormality is particularly useful for a specimen processing system in which a plurality of preprocessing units and analysis units, etc. are connected through a transfer line.

Also, there is further provided the communication part 3b which outputs the sensor signal waveform information before or after the occurrence of the operation abnormality to the side of the maintenance person who maintains the specimen processing system 100 when it is determined in the abnormality detecting part 3a that the abnormality has occurred. Therefore, it is possible to confirm the state of the presence/absence of the abnormality in the sensor signal waveform before or after the device alarm from the location away from the device. It is not necessary to go to the location where the specimen processing device is mounted, for the purpose of analyzing the device abnormality. Consequently, the time taken for the analysis of the device abnormality can be greatly shortened, and the non-operating time in the specimen processing system can be greatly shortened.

Further, the recording device is comprised of the recording memory 9a which sequentially records the signal waveforms, and the recording medium 9b provided separately from the recording memory 9a which stores the sensor signal waveform before or after the occurrence of the operation abnormality. Thus, since it is possible to more accurately and simply acquire the information about the device abnormality, the time necessary for the state restoration can be more shortened. Moreover, the effect of making it possible to easily construct the configuration of storing the sensor signal waveform before or after the occurrence of the operation abnormality in the unerasable area is also brought about.

Also, when the recording capacity is full, the recording memory 9a erases the sensor signal waveform other than the sensor signal waveform before or after the occurrence of the operation abnormality stored when it is determined that the abnormality has occurred, thereby making it possible to provide a low-cost specimen processing system without the need to use a large capacity recording memory more than necessary.

Moreover, there is further provided the AD converter 8 which converts the signal waveform from analog to digital. The recording device records and stores the signal waveform after being converted to the digital by the AD converter 8. Consequently, the confirmation of the sensor signal waveform at the time of the occurrence of the device alarm becomes easier, and the time necessary for the state restoration can be more shortened.

Incidentally, the present embodiment has described the case where the recording medium 9b and the recording memory 9a are disposed at positions physically away from each other, but is not limited thereto. The recording device can be realized by the same device.

Second Embodiment

Figure 5:
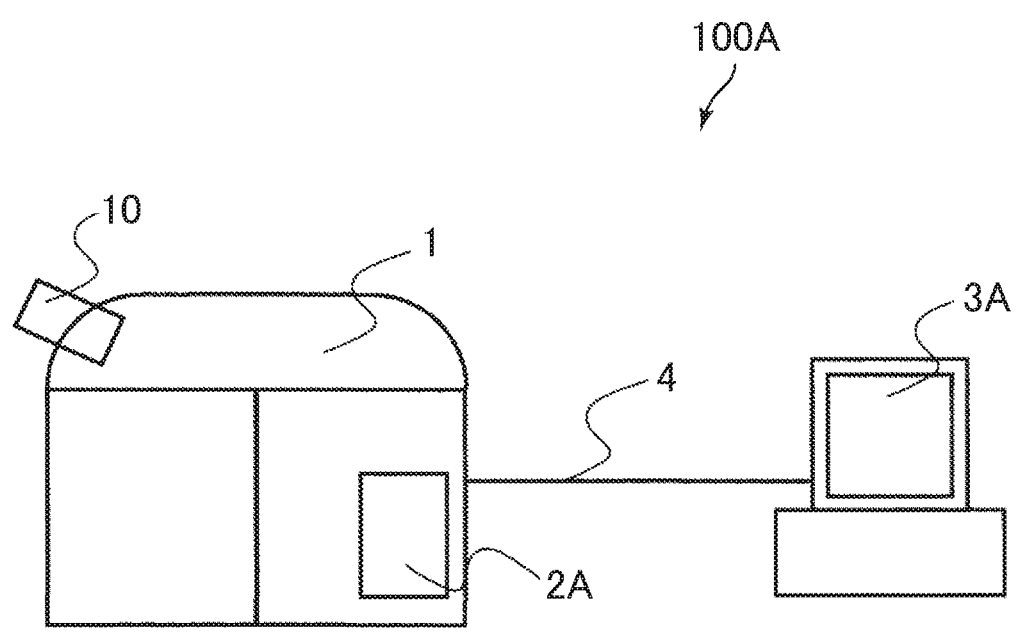
FIG. 5 is a typical diagram of a specimen processing device having a sensor signal observing function and a video recording function according to a second embodiment of the present invention.
Figure 6:
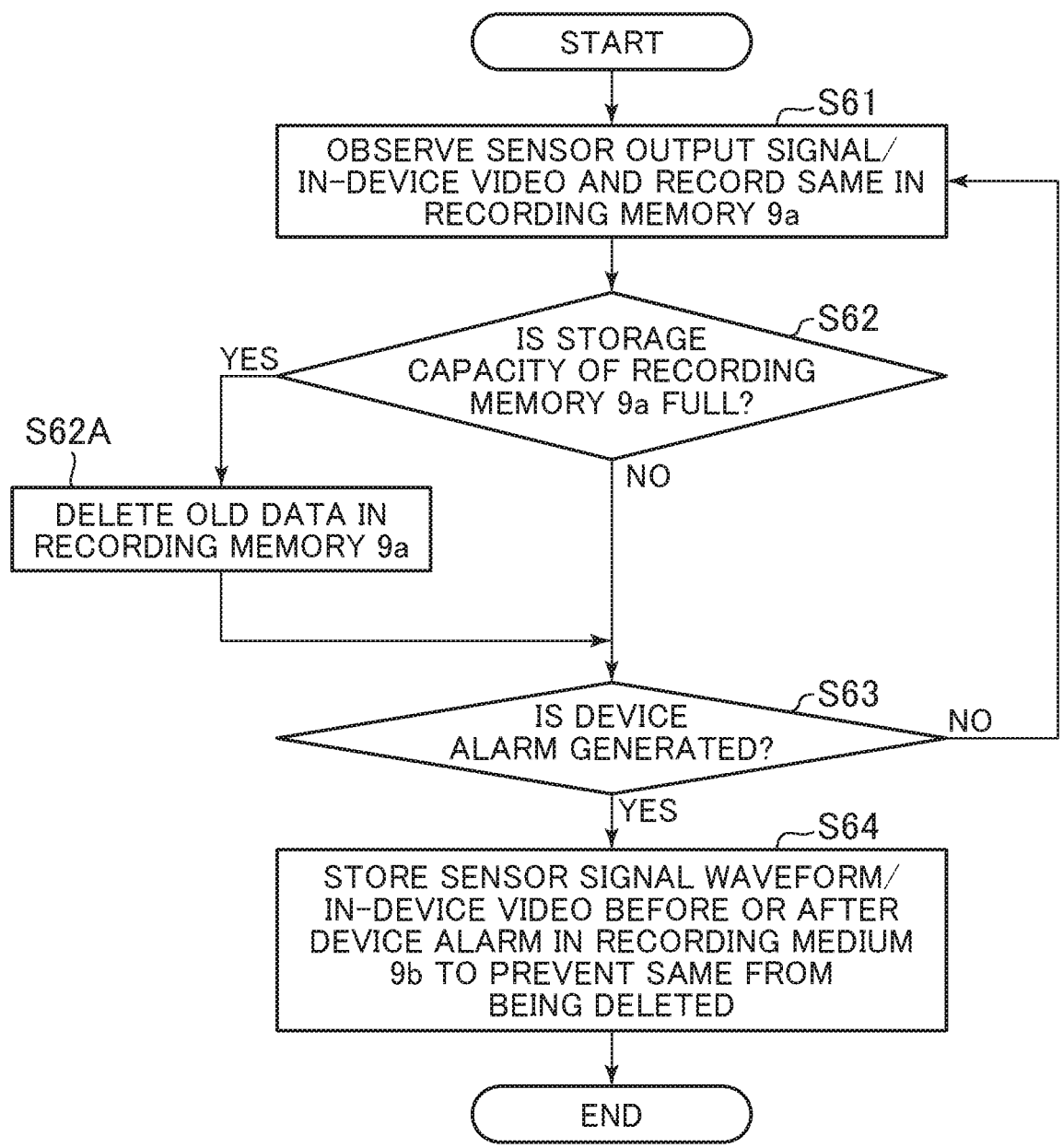
FIG. 6 is a diagram showing a processing flow of the specimen processing device according to the second embodiment.

A specimen processing system according to a second embodiment of the present invention will be described using FIG. 5 and FIG. 6. FIG. 5 is a typical diagram of a specimen processing device according to the present embodiment. FIG. 6 is a diagram showing a processing flow of the specimen processing device according to the present embodiment.

Incidentally, the same configurations as the first embodiment will be given the same numerals, and description thereof will be omitted. The same applies to the following embodiments too.

As shown in FIG. 5, the specimen processing system 100A according to the present embodiment includes an imaging device 10 in addition to a specimen processing device 1, a sensor signal observing substrate 2A, an operation unit PC3A, a communication connection line 4, etc.

The imaging device 10 is a device which captures a prescribed location in the specimen processing system 100A, and detects, together with sensors 5a, 5b, . . . , a driving state of the specimen processing device 1.

The imaging device 10 in the present embodiment is a camera for imaging the manner of transfer of a specimen container 220 storing a specimen therein, and a driving state of a driving device, and recording the same as an video image. The imaging device 10 is disposed at a position where it can image the operation of a mechanism system of the specimen processing device 1 and the specimen container 220, and in synchronism with a signal observing function of each of the sensors 5a, 5b, . . . , the imaging device 10 images an object.

A recording memory 9a in the present embodiment sequentially records images captured by the imaging device 10 as well. Further, a recording medium 9b also stores an image before or after the occurrence of an operation abnormality in an unerasable area when it is determined in an abnormality detecting part 3a that the abnormality has occurred. Since the recoding memory 9a and the recording medium 9b in the present embodiment record image information as well, it is desirable that a recording capacity is larger than that in the first embodiment.

Next, the operation of the specimen processing system according to the present embodiment will be described with reference to FIG. 6. FIG. 6 is a processing flow of the specimen processing device having the sensor signal observing function according to the present invention.

First, in FIG. 6, the specimen processing device 1 observes sensor signal waveforms by the sensors 5a, 5b, . . . of the sensor signal observing substrate 2A and also acquires in-device video information by the imaging device 10, and records the sensor signal waveforms in the recording memory 9a (Step S61).

Next, the sensor signal observing substrate 2A determines whether or not the recording capacity of the recording memory 9a is full (Step S62). When it is determined that the recording capacity is full, the processing is advanced to Step S62A, where old data in the recording memory 9a is deleted to ensure a recordable area (Step S62A). These Steps S62 and S62A are the same processing as those in Step S52 and Step S52A shown in FIG. 4. On the other hand, when it is determined that the recording memory 9a is not full, the processing is advanced to Step S63 without deleting the data.

Next, the abnormality detecting part 3a of the operation unit PC3A determines whether it is necessary to generate a device alarm with the occurrence of an abnormality in each driving device in the specimen processing device 1 (Step S63). When it is determined that the device alarm is not necessary, the processing is returned to Step S61, where the observation of each sensor signal waveform and video observation by the imaging device 10 are continuously performed.

On the other hand, when it is determined in Step S63 that the device alarm has occurred, the processing is advanced to Step S64, where the specimen processing device 1 is controlled through the communication connection line 4 to store the sensor signal waveform before or after the device alarm recorded in the recording memory 9a, and the captured image of the imaging device 10 in the recording medium 9b being an undeleted area (Step S64). An operator acquires the stored data through the operation unit PC3A and uses it upon executing the analysis of an abnormality in the device.

Other configurations/operations are almost the same as those in the above-described specimen processing system 100 according to the first embodiment, and the details thereof will be omitted.

Even in the specimen processing system 100A according to the second embodiment of the present invention, effects substantially similar to those in the aforementioned specimen processing system 100 according to the first embodiment are obtained.

Further, the sensor includes the imaging device 10 which images a prescribed location in the specimen processing system 100A. The recording device sequentially records the images captured by the imaging device 10 and stores the image before or after the occurrence of the operation abnormality in the unerasable area when it is determined in the abnormality detecting part 3a that the abnormality has occurred. Consequently, it becomes unnecessary to perform observation and imaging by reproducing the same operation. Thus, the time necessary for abnormality analysis of the device can be more shortened, and the non-operating time of the specimen processing system 100A can be more shortened.

Further, the imaging device 10 is the camera which images the manner of transfer of the specimen container 220 storing the specimen therein, and the driving state of the driving device. Therefore, the state of the presence/absence of the abnormality in the specimen transfer information can also be confirmed.

Incidentally, although description has been made as to the case where the imaging device 10 images the manner of transfer of the specimen container 220 storing the specimen therein, and the driving state of the driving device, the imaging device 10 is not limited thereto and may be one which images a prescribed location in the specimen processing system 100A.

Third Embodiment

Figure 7:
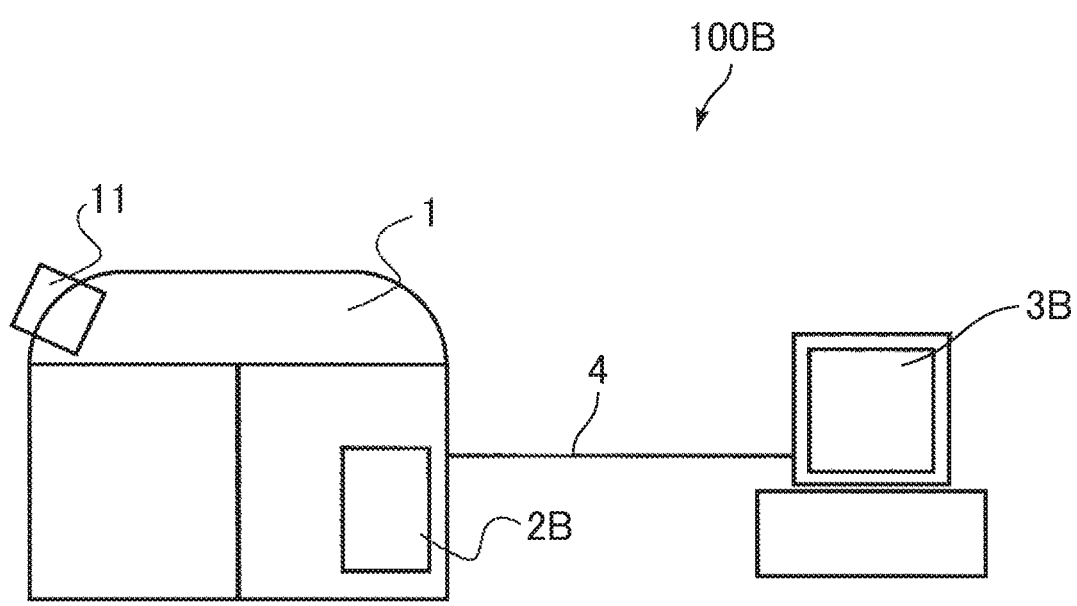
FIG. 7 is a typical diagram of a specimen processing device having a sensor signal observing function and a specimen position grasping function according to a third embodiment of the present invention.
Figure 8:
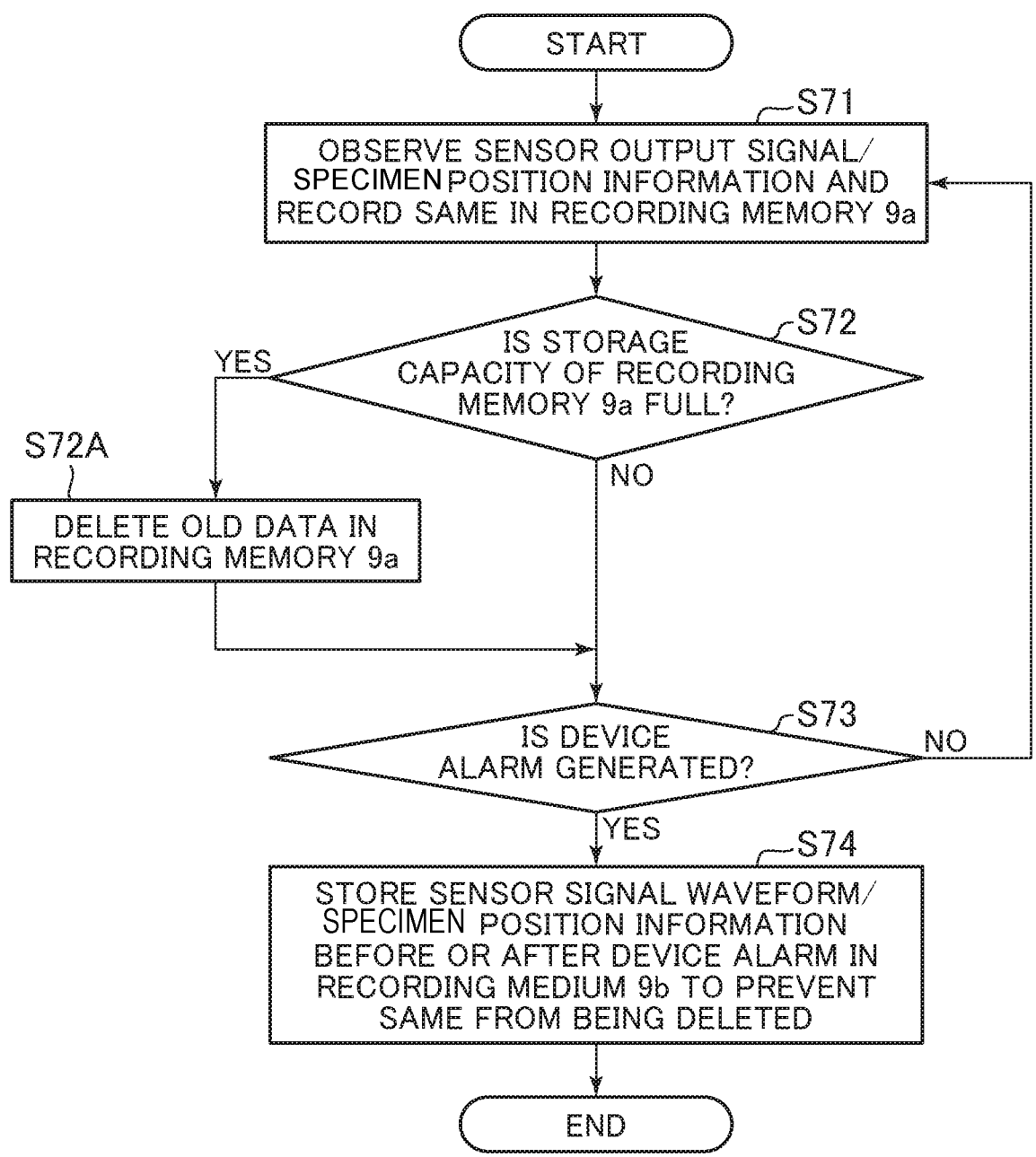
FIG. 8 is a diagram showing a processing flow of the specimen processing device according to the third embodiment.

A specimen processing system according to a third embodiment of the present invention will be described using FIG. 7 and FIG. 8. FIG. 7 is a typical diagram of a specimen processing device in the present embodiment. FIG. 8 is a diagram showing a processing flow of the specimen processing device in the present embodiment.

As shown in FIG. 7, the specimen processing system 100B according to the present embodiment includes a specimen position grasping device 11 in addition to a specimen processing device 1, a sensor signal observing substrate 2B, an operation unit PC3B, a communication connection line 4, etc.

The specimen position grasping device 11 is a device which acquires specimen information (information about the external appearance of a specimen and its in-device position) in the specimen processing system 100B, and detects, together with sensors 5a, 5b, . . . , a driving state of the specimen processing device 1.

The specimen position grasping device 11 in the present embodiment is at least any one or more of a thermography camera which images a specimen container 220 storing the specimen therein and an RFID reader which acquires information of an RFID tag attached to the specimen container 220.

If the thermography camera is adopted, it is capable of grasping the position and movement of a specimen such as blood, urine or the like by recognizing the temperature of the specimen.

In the case of the RFID, it is capable of grasping the position of the specimen in the device by reading the RFID tag loaded on a rack or a holder with the specimen placed thereon. It is thus possible to clearly grasp the position information of the specimen in the device.

The specimen position grasping device 11 such as the thermography camera, the RFID or the like is disposed at a position where it can grasp the position of the specimen such as blood, urine or the like in the specimen processing device 1, and in synchronism with a signal observing function of each of the sensors 5a, 5b, . . . , the specimen position grasping device 11 acquires specimen information.

A recording memory 9a in the present embodiment sequentially records the specimen information acquired in the specimen position grasping device 11 as well. Further, a recording medium 9b also stores specimen information before or after the occurrence of an operation abnormality in an unerasable area when it is determined in an abnormality detecting part 3a that the abnormality has occurred. Even in regard to the recoding memory 9a and the recording medium 9b in the present embodiment, it is desirable that a recording capacity is larger than that in the first embodiment.

Next, the operation of the specimen processing system according to the present embodiment will be described with reference to FIG. 8. FIG. 8 is a processing flow of the specimen processing device having the sensor signal observing function according to the present invention.

First, in FIG. 8, the specimen processing device 1 observes sensor signal waveforms by the sensors 5a, 5b, . . . of the sensor signal observing substrate 2B and also acquires specimen information by the specimen position grasping device 11, and records the sensor signal waveforms in the recording memory 9a (Step S71).

Next, the sensor signal observing substrate 2B determines whether or not the recording capacity of the recording memory 9a is full (Step S72). When it is determined that the recording capacity is full, the processing is advanced to Step S72A, where old data in the recording memory 9a is deleted to ensure a recordable area (Step S72A). These Steps S72 and S72A are the same processing as those in Step S52 and Step S52A shown in FIG. 4. On the other hand, when it is determined that the recording memory 9a is not full, the processing is advanced to Step S73 without deleting the data.

Next, the abnormality detecting part 3a of the operation unit PC3B determines whether it is necessary to generate a device alarm with the occurrence of an abnormality in each driving device in the specimen processing device 1 (Step S73). When it is determined that the device alarm is not necessary, the processing is returned to Step S71, where the observation of each sensor signal waveform and observation by the specimen position grasping device 11 are continuously performed.

On the other hand, when it is determined in Step S73 that the device alarm has occurred, the processing is advanced to Step S74, where the specimen processing device 1 is controlled through the communication connection line 4 to store the sensor signal waveform before or after the device alarm and the specimen information recorded in the recording memory 9a in the recording medium 9b being an undeleted area (Step S74). An operator acquires the stored data through the operation unit PC3B and uses it when executing the analysis of an abnormality in the device.

Other configurations/operations are almost the same as those in the above-described specimen processing system 100 according to the first embodiment, and the details thereof will be omitted.

Even in the specimen processing system 100B according to the third embodiment of the present invention, effects substantially similar to those in the aforementioned specimen processing system 100 according to the first embodiment are obtained.

Further, the sensors 5a, 5b, . . . respectively include the specimen position grasping device 11 which acquires specimen information in the specimen processing system 100B. The recording device sequentially records the specimen information acquired in the specimen position grasping device 11 and stores the specimen information before or after the occurrence of the operation abnormality in the unerasable area when it is determined in the abnormality detecting part 3a that the abnormality has occurred. Consequently, it becomes unnecessary to confirm the position of the specimen by reproducing the same operation and it is possible to more shorten the time necessary for abnormality analysis of the device, thereby making it possible to more effectively shorten the non-operating time in the specimen processing system.

Further, the specimen position grasping device 11 is at least either the thermography camera which images the specimen container 220 storing the specimen therein or the RFID reader which acquires the information of the RFID tag attached to the specimen container 220, thereby making it possible to accurately and simply grasp the specimen information.

Fourth Embodiment

Figure 9:
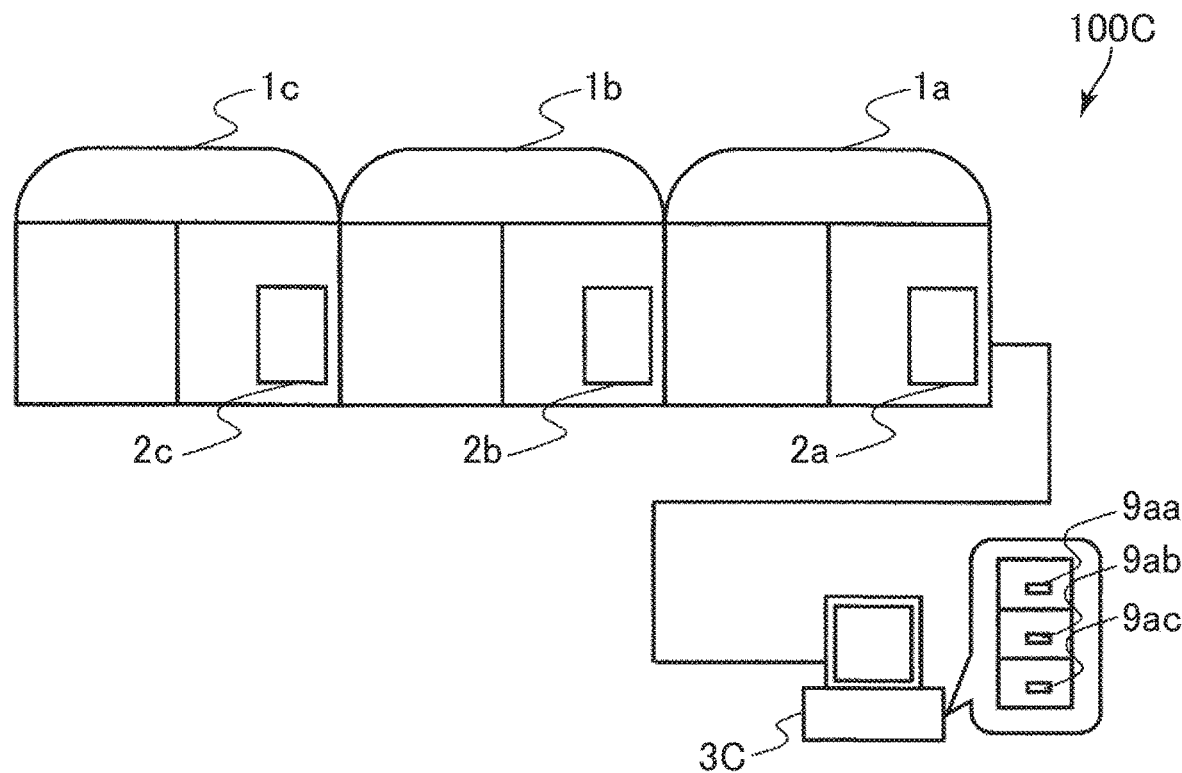
FIG. 9 is a typical diagram of a specimen processing system comprised of a plurality of specimen processing devices each having a sensor signal observing function according to a fourth embodiment of the present invention.

A specimen processing system according to a fourth embodiment of the present invention will be described using FIG. 9. FIG. 9 is a typical diagram of the specimen processing system according to the present embodiment, which is comprised of a plurality of specimen processing devices.

As shown in FIG. 9, the specimen processing system 100C according to the present embodiment has the plurality of specimen processing devices $1a$, $1b$, $1c$, .... Any of these specimen processing devices $1a$, $1b$, $1c$, ... is an automatic analyzer which performs a biochemical analysis, an immune analyzer which performs an immunological analysis, or a specimen preprocessing device connected to the automatic analyzer and the immune analyzer such as shown in FIG. 2.

In the plural specimen processing devices $1a$, $1b$, $1c$, ..., sensor signal observing substrates $2a$, $2b$, $2c$, ... are installed independently in the respective devices.

Also, in the present embodiment, the whole of recording devices each including a recording memory $9a$ is disposed within an operation unit PC3C. In addition, the recording devices in the present embodiment include storage areas divided for each device into areas where sensor signal waveform information can be classified for $1a$, $1b$, $1c$, ... of each specimen processing device (recording memories $9aa$, $9ab$, $9ac$). The respective storage areas are linked to the respective specimen processing devices $1a$, $1b$, $1c$, ... on one-to-one basis. Consequently, the sensor signal waveforms are classified and recorded.

The specimen processing system 100C according to the present embodiment always perform observation by means of the senor signal observing substrates $2a$, $2b$, $2c$, ... of the respective devices and records observation results in the recording memories $9aa$, $9ab$, and $9ac$.

Thereafter, when the recording capacities of the recording memories $9aa$, $9ab$, and $9ac$ are full in a manner similar to the first embodiment or the like, old data in the recording memories $9aa$, $9ab$, and $9ac$ are deleted to ensure recordable areas.

Further, the operation unit PC3C determines the presence/absence of a device alarm. When the device alarm is absent, the sensor signal waveforms are continuously observed. When the device alarm has occurred, the respective device sensor signal waveforms before and after the alarm are recorded in undeleted areas.

Other configurations/operations are almost the same as those in the above-described specimen processing system 100 according to the first embodiment, and the details thereof will be omitted.

Even in the specimen processing system 100C according to the fourth embodiment of the present invention, effects substantially similar to those in the aforementioned specimen processing system 100 according to the first embodiment are obtained.

Fifth Embodiment

A specimen processing system according to a fifth embodiment of the present invention will be described using FIG. 10.

Figure 10:
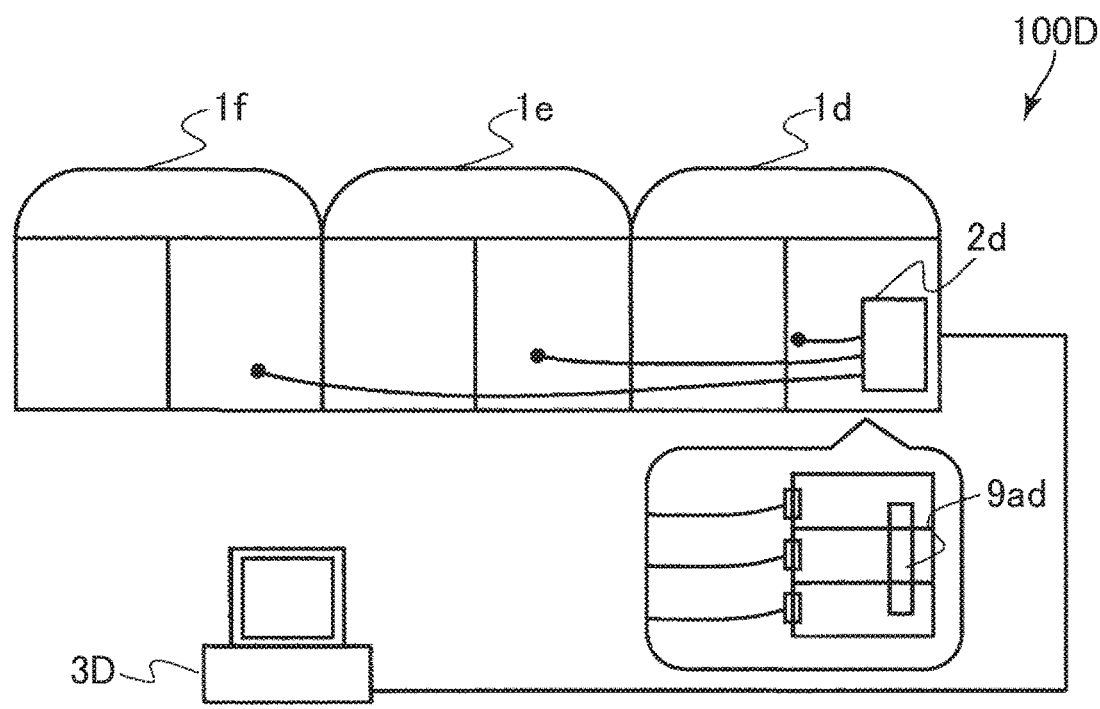
FIG. 10 is a typical diagram of a specimen processing system including one specimen processing device having a sensor signal observing function according to a fifth embodiment of the present invention.

As shown in FIG. 10, the specimen processing system 100D according to the present embodiment has a plurality of specimen processing devices $1d$, $1e$, $1f$, .... Any of these specimen processing devices $1d$, $1e$, $1f$, ... is an automatic analyzer which performs a biochemical analysis, an immune analyzer which performs an immunological analysis, or a specimen preprocessing device connected to the automatic analyzer and the immune analyzer such as shown in FIG. 2.

In the plural specimen processing devices $1d$, $1e$, $1f$, ... in the present embodiment, a sensor signal observing substrate $2d$ having a function of classifying and obtaining sensor signal waveforms of the specimen processing devices $1d$, $1e$, $1f$, ... is mounted in the specimen processing device $1d$ as distinct from the fourth embodiment.

The sensor signal observing substrate $2d$ is a cartridge type and acquires sensor signal waveforms of the targeted specimen processing devices $1d$, $1e$, $1f$, ... in correspondence with the place of an inserted cartridge. If such a configuration is taken, it is possible to acquire the sensor signal waveform of each of the specimen processing devices $1d$, $1e$, $1f$, ..., which is desired to obtain, and to acquire sensor signal waveform information by detaching the inserted cartridge.

A recording memory $9ad$ having storage areas divided into areas where the sensor signal waveform information every specimen processing devices $1d$, $1e$, $1f$, ... can be classified, is disposed in the sensor signal observing substrate $2d$. The signal waveforms of the plural specimen processing devices $1d$, $1e$, $1f$, ... are integrated and sequentially recorded.

The specimen processing system 100D according to the present embodiment always perform observation by means of the senor signal observing substrate $2d$ of the specimen processing device $1d$ and records a result of its observation in the recording memory $9ad$.

Thereafter, when the recording capacity of the recording memory $9ad$ is full in a manner similar to the first embodiment or the like, old data in the recording memory $9ad$ is deleted to ensure a recordable area.

Further, an operation unit PC3D determines the presence/absence of a device alarm. When the device alarm is absent, the sensor signal waveforms are continuously observed. When the device alarm has occurred, the respective device sensor signal waveforms before and after the alarm are recorded in undeleted areas.

Other configurations/operations are almost the same as those in the above-described specimen processing system 100 according to the first embodiment, and the details thereof will be omitted.

Even in the specimen processing system 100D according to the fifth embodiment of the present invention, effects substantially similar to those in the aforementioned specimen processing system 100 according to the first embodiment are obtained.

Others

Incidentally, the present invention is not limited to the above-described embodiments and includes various modifications. The above-described embodiments have been described in detail to describe the present invention in an easy to understand manner, and are not necessarily limited to those having all configurations described here.

Also, a part of the configuration of one embodiment can also be replaced with the configuration of another embodiment. Further, the configuration of another embodiment can also be added to the configuration of one embodiment. Moreover, addition, deletion and replacement of another configuration can be performed to the part of the configuration of each embodiment.

LIST OF REFERENCE SIGNS

1, $1a$, $1b$, $1c$, $1d$, $1e$, $1f$ ... specimen processing device (processing unit),
2, 2A, 2B, $2a$, $2b$, $2c$, $2d$ ... sensor signal observing substrate, 3, 3A, 3B, 3C, 3D ... operation unit PC,
3a ... abnormality detecting part,
3b ... communication part,
4 ... communication connection line,
5a, 5b ... sensor,
6a, 6b ... comparator,
7a, 7b ... control IC,
8a, 8b ... AD converter,
9a, 9aa, 9ab, 9ac, 9ad ... recording memory (recording device, first recording unit),
9b ... recording medium (recording device, second recording unit),
10 ... imaging device,
11 ... specimen position grasping device (specimen position acquiring device),
20 ... maintenance person side display device,
100, 100A, 100B, 100C, 100D ... specimen processing system,
102 ... closing unit,
103 ... specimen storage unit,
104 ... holder stacker,
105 ... specimen input unit,
106 ... centrifugal unit,
107 ... liquid amount measuring unit,
108 ... opening unit,
109 ... child specimen test-tube preparation unit,
110 ... dispensing unit,
111 ... transfer unit
200 ... automatic analyzer,
204 ... reaction container,
205 ... reaction disk mechanism,
207 ... thermostatic tank,
208 ... reagent bottle,
209 ... reagent magazine,
210 ... specimen dispensing mechanism,
211 ... reagent dispensing mechanism,
212 ... stirring mechanism,
213 ... cleaning mechanism,
214 ... light source,
215 ... photometer,
216 ... A/D converter,
220 ... specimen container, child specimen container.

The invention claimed is:

1. A specimen processing system, including a specimen processing device, which is configured to perform preprocessing and analysis of a specimen, comprising:
sensors each configured to detect a driving state of a driving device installed in the system; and
an abnormality detecting part configured to determine from signal waveforms detected by the sensors whether an abnormality occurs in the driving device,
wherein the specimen processing system includes a recording device which is configured to sequentially record the signal waveforms detected by the sensors, and configured to store a sensor signal waveform before or after the occurrence of an operation abnormality when the abnormality is determined to have occurred in the abnormality detecting part,
wherein the sensors include a specimen position acquiring device which is configured to acquire specimen information in the specimen processing system,
wherein the recording device is configured to sequentially record the specimen information acquired in the specimen position acquiring device, and configured to store specimen information before or after the occurrence of an operation abnormality when the abnormality is determined to have occurred in the abnormality detecting part, and
wherein the recording device is configured to store the specimen information into an unerasable area, and the specimen position acquiring device is configured to detect, together with the sensors, a driving state of the specimen processing device.

2. The specimen processing system according to claim 1, wherein the sensor includes an imaging device which is configured to image a prescribed location in the specimen processing system, and
wherein the recording device is configured to sequentially record images captured by the imaging device, and is configured to store an image before or after the occurrence of an operation abnormality into an unerasable area when the abnormality is determined to have occurred in the abnormality detecting part.

3. The specimen processing system according to claim 2, wherein the imaging device is a camera which is configured to image the manner of transfer of a specimen container storing a specimen therein, and the driving state of the driving device.

4. The specimen processing system according to claim 1, further including a communication part which is configured to output sensor signal waveform information before or after the occurrence of the operation abnormality to the side of a maintenance person who maintains the specimen processing system when the abnormality is determined to have occurred in the abnormality detecting part.

5. The specimen processing system according to claim 1, wherein the specimen processing system has a plurality of processing units, and
wherein the plural processing units are respectively provided with the recording device independently of each other.

6. The specimen processing system according to claim 1, wherein the specimen processing system has a plurality of processing units, and
wherein the recording device is configured to integrate and sequentially record sensor signal waveforms of the plural processing units.

7. The specimen processing system according to claim 1, wherein the recording device is comprised of a first recording unit which is configured to sequentially record signal waveforms, and a second recording unit provided separately from the first recording unit, the second recording unit is configured to store a sensor signal waveform before or after the occurrence of an operation abnormality.

8. The specimen processing system according to claim 1, wherein when a recording capacity of the recording device is full, the recording device is configured to erase a sensor signal waveform other than the sensor signal waveform before or after the occurrence of the operation abnormality, which is stored when the abnormality is determined to have occurred.

9. The specimen processing system according to claim 1, further including an AD converter which is configured to convert the signal waveform from analog to digital,
wherein the recording device is configured to record and stores a signal waveform after being converted to digital by the AD converter.

10. The specimen processing system according to claim 1, wherein the specimen position acquiring device is at least any one or more of a thermography camera which is configured to image a specimen container storing a specimen, and an RFID reader which is configured to acquire information of an RFID tag attached to the specimen container.

* * * * *